(12) United States Patent
Wicks et al.

(10) Patent No.: US 7,001,719 B2
(45) Date of Patent: Feb. 21, 2006

(54) DEVICES AND METHODS FOR MICROORGANISM DETECTION

(75) Inventors: James H. Wicks, Oakdale, MN (US); Carl A. Adams, Apple Valley, MN (US); Gary E. Krejcarek, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/818,092

(22) Filed: Apr. 5, 2004

(65) Prior Publication Data
US 2004/0191892 A1 Sep. 30, 2004

Related U.S. Application Data

(62) Division of application No. 09/434,586, filed on Nov. 5, 1999, now Pat. No. 6,737,266.

(60) Provisional application No. 60/157,237, filed on Oct. 1, 1999.

(51) Int. Cl.
*C12Q 1/70* (2006.01)

(52) U.S. Cl. ........................................................ 435/5

(58) Field of Classification Search ................ 435/5, 435/288.2, 287.6, 288.1; 422/58, 59
See application file for complete search history.

(56) References Cited

U.S. PATENT DOCUMENTS

| | | | |
|---|---|---|---|
| 3,290,017 A | 12/1966 | Davies et al. | |
| 4,364,474 A | 12/1982 | Hollander, Jr. | 206/219 |
| 4,632,244 A | 12/1986 | Landau | 206/219 |
| 4,690,801 A | 9/1987 | Anderson | 422/68 |
| 4,770,853 A | 9/1988 | Bernstein | 422/102 |
| 4,939,152 A | 7/1990 | Barr et al. | 435/296 |
| 5,067,051 A | 11/1991 | Ladyjensky | 362/34 |
| 5,403,622 A | 4/1995 | Nishi et al. | 427/356 |
| 5,498,525 A | 3/1996 | Rees et al. | 435/29 |
| 5,508,893 A | 4/1996 | Nowak et al. | 362/34 |
| 5,552,968 A | 9/1996 | Ladyjensky | 362/34 |
| 5,573,951 A | 11/1996 | Gombrich et al. | 435/287.3 |
| 5,840,308 A | 11/1998 | Jassim et al. | 424/195.1 |
| 5,958,675 A | 9/1999 | Wicks et al. | 206/219 |
| 6,189,688 B1 | 2/2001 | Aneas | |

FOREIGN PATENT DOCUMENTS

| | | |
|---|---|---|
| EP | 0 986 792 A1 | 2/1999 |
| WO | WO 94/26414 | 11/1994 |
| WO | WO 95/22254 | 8/1995 |

OTHER PUBLICATIONS

Graham, "Timely Test Spots TB 'in hours'," New Scientist, p. 21, (Aug. 17, 1996).

*Primary Examiner*—David Redding
(74) *Attorney, Agent, or Firm*—Daniel R. Pastirik

(57) ABSTRACT

A device that includes at least two chambers separated by an activatable seal wherein upon activation of the seal the two chambers are in communication, and further wherein at least one chamber of the device includes a biological assay reagent and methods of using same.

4 Claims, 1 Drawing Sheet

DEVICES AND METHODS FOR MICROORGANISM DETECTION

CROSS-REFERENCE TO RELATED APPLICATIONS

This application is a division of U.S. patent application Ser. No. 09/434,586, filed Nov. 5, 1999 now U.S. Pat. No. 6,737,266 which invention claims priority to U.S. Provisional Patent Application Ser. No. 60/157,237, filed on Oct. 1, 1999 and entitled DEVICES AND METHODS FOR MICROORGANISM DETECTION, which is incorporated herein by reference.

FIELD OF THE INVENTION

This invention relates to the detection of microorganisms and more particularly to self-contained assay devices and methods of use for the detection and enumeration of microorganisms in a variety of samples such as foods, clinical specimens, and environmental samples.

BACKGROUND

Detection of microorganisms, particularly bacteria, is important in a variety of industries, including the food and beverage industry. For example, the need to screen food and water for pathogenic bacteria is crucial to ensuring consumer safety. The determination of levels of certain families of bacteria is a commonly used approach to estimating the shelf life and microbial acceptability of food products and hygienic status of the processing equipment and raw materials used in their manufacture. The diagnosis of microbial infections also relies on the detection of the causative organism(s).

There are many methods known for detecting bacteria. For example, bacteriophage, which are viruses that infect bacteria, may be employed. The presence of the bacteriophage, the infected bacteria, or the lack thereof, may be detected. These known methods suffer from various drawbacks. For example, the sample to be tested or equipment used may be contaminated during the handling of the sample. Another problem involves ease of use of the associated detection device. Still another problem encountered is the time it takes to detect a microorganism. Yet another potential problem involves containment of the components of the assay, such as for example, phage or helper bacteria, to prevent certain infection of the surrounding environment.

SUMMARY

This invention provides devices and methods that help minimize handling concerns of assays for the detection of microorganisms, particularly bacteria. The devices and methods are relatively easy to use. In a preferred embodiment of the present invention, the methods and devices use phage amplification for relatively rapid and accurate results. Thus, using the devices and methods of the present invention, microorganism detection may be conducted in a self-contained, easy to use unit that provides relatively rapid and accurate results.

In one aspect, the invention provides a device comprising at least two chambers separated by an activatable seal wherein upon activation of the seal the two chambers are in communication. Preferably, the activation can occur by rotating (e.g., tilting) the seal, crushing the seal, or otherwise gating or opening the seal. At least one chamber of the device includes a biological assay reagent.

In another aspect, the invention provides a device comprising at least two chambers separated by an activatable seal, wherein at least one chamber includes a biological assay reagent comprising bacteriophage, an antiviral agent, or bacterial helper cells.

In another aspect, the invention provides a device comprising at least three chambers, each of which is separated by a rotatable seal, wherein a first chamber includes bacteriophage, a second chamber includes an antiviral agent, and a third chamber includes bacterial helper cells. Preferably, the second chamber is disposed between the first and third chambers and is separated into two subchambers separated from each other by a rotatable seal, wherein each subchamber includes a different antiviral agent.

In yet another aspect, the invention provides a method for detecting the presence or absence of a microorganism, the method comprising: providing a device comprising at least two chambers separated from each other by an activatable seal, wherein at least one chamber includes a biological assay reagent; adding a sample suspected of including the microorganism to at least one of the chambers; activating the seal between one or more of the chambers to allow contact between the reagent and the sample; and detecting the presence or absence of the microorganism in the sample.

In still another aspect, the invention provides a method for detecting the presence or absence of bacteria, the method comprising: providing a device comprising at least three chambers separated from each other by activatable seals, wherein a first chamber includes bacteriophage, a second chamber includes an antiviral agent, and a third chamber includes bacterial helper cells, wherein the second chamber is disposed between the first and third chambers; adding a sample suspected of including a target bacteria to the first chamber comprising bacteriophage; allowing the bacteriophage to infect the target bacteria; activating the seal between the first and second chambers to allow contact between the antiviral agent and extracellular bacteriophage; activating the seal between the second and third chambers to allow contact between the bacterial helper cells and the infected target bacteria; incubating the bacterial helper cells and the infected bacteria; and detecting the presence or absence of the target bacteria in the sample.

DETAILED DESCRIPTION OF PREFERRED EMBODIMENTS

Figure 1:
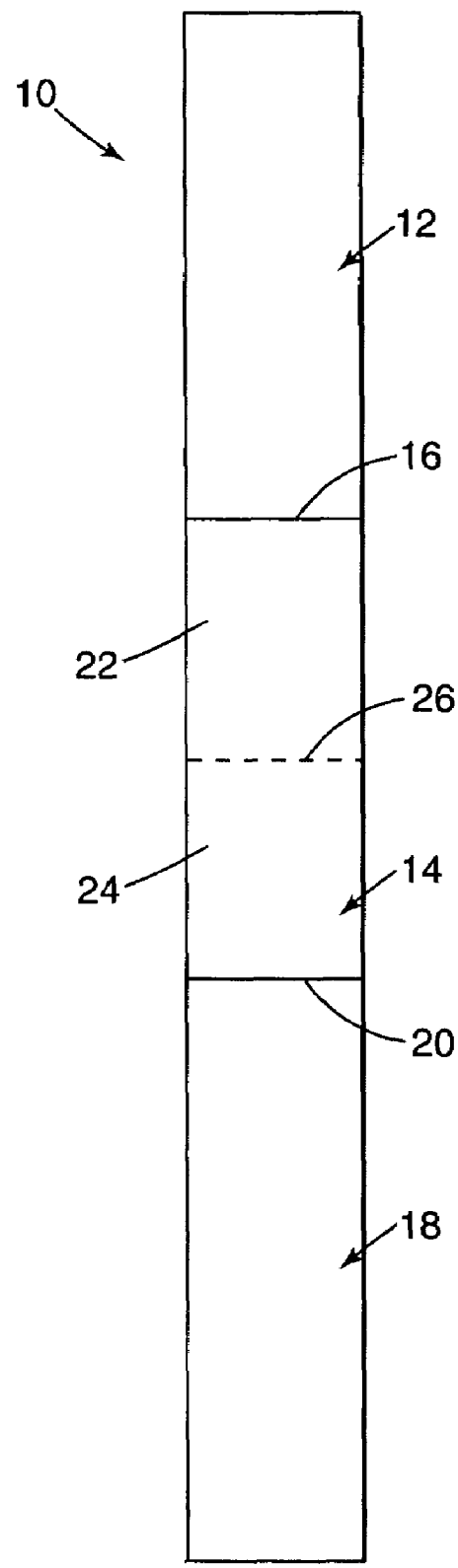
FIG. 1 is a schematic of a preferred embodiment of a device of the present invention.

The present invention includes methods and devices for detecting a microorganism (e.g., bacteria, yeast, fungi, and viruses such as bacteriophage), particularly bacteria. In a preferred embodiment, the invention relates to the use of phage amplification to detect bacteria. In one aspect, the method incorporates the use of a device having at least two chambers separated by an activatable seal (i.e., a component, such as a valve, that separates two compartments so as to prevent leakage) wherein upon activation of the seal, the two chambers are in communication. Preferably, this device is in the form of a tube, which can have a variety of cross-sectional shapes, although other constructions (e.g., rectangular or circular tubes, channels on a flat substrate, or microreplicated structures) are envisioned. This device reduces the potential contamination of the sample. Furthermore, it is convenient and easy to use as it is self-contained.

Preferred embodiments of the devices and methods of the invention exploit the interaction between bacteriophage and bacteria. They can be used for the testing and detection of bacteria or bacteriophage in a sample, for determining the susceptibility of bacteria to antibacterial agents, and/or for determining the effectiveness of virucidal agents. Both qualitative and quantitative testing can be carried out. Methods such as those described in U.S. Pat. No. 5,498,525 (Rees et al.) may be performed using the devices and methods of the present invention.

Preferred methods of the invention are based on the specific recognition/binding relationship that results when a bacteriophage infects a bacterium. The bacteriophage injects its nucleic acid into the host bacterium, which is then used to replicate the "phage" being produced and, upon breaking open the host, to then infect additional bacteria (e.g., helper bacteria). Once the phage has specifically infected the cell and injected its nucleic acid, it is protected from the extracellular environment. Thus, those phages which have not specifically infected a bacterium can be killed. The removal or killing of unbound phage can be achieved by a variety of methods. These include, for example, the use of virucidal agents or heat, or removal of chemicals essential for phage stability. The number of bacteriophage protected and able to replicate and emerge may be sufficient to be detected directly. Alternatively, the number can be amplified by growing them on a propagating host for the required time (this can be short since phage generation times are less than 1 hour and 10–1000 progeny are produced). While the above describes phage exhibiting a lytic pathway, one of skill in the art will recognize that lysogenic phage can also be employed in the methods and devices of the present invention.

Detection of the phage can be carried out by a number of methods. These include, for example, immunologic methods using an antibody to some component of the phage, methods using a nucleic acid probe to the phage genome, or by plaque assay. Alternatively, detection can involve turbidity changes, plaque formation, as well as color, luminescence, or fluorescence changes. One method is based on the discovery that a bacterium can be constructed by genetic modification that has the potential to produce a detectable signal (gene(s) coding for a phenotype that can be readily detected) when the bacterium is infected by a phage. The phage triggers the signal generation and hence the presence of the phage (and therefore of the bacterium that protected it) can be detected sensitively and easily. These bacteria, referred to as reporter bacteria, are described in greater detail in U.S. Pat. No. 5,498,525 (Rees et al.).

In a preferred embodiment, the device is used in the detection of bacteria (target bacteria). This is done by adding bacteriophage to a test sample to infect the target bacteria in the test sample, killing the extracellular bacteriophage with an antiviral (or mixture of antivirals), neutralizing the antiviral (for example, with a buffer), and amplifying the bacteriophage, thereby facilitating plaque formation and detection from the phage-infected target bacteria with the aid of a lawn of bacterial helper cells. This phage lytic cycle in bacteria with plaque formation as the end-point is hereinafter referred to as "Phage Amplification Assay" (PAA). Relative amounts of the various reagents used in such an assay are known to those of skill in the art and are disclosed in U.S. Pat. No. 5,498,525 (Rees et al.). The assay results of plaque formation can be read rapidly, typically within about four hours to about six hours, and confirming at 24 hours, if needed. Conventional methods to enumerate bacteria usually require about 24 hours to about 48 hours of growth.

Suitable bacteriophage for detection of target bacteria include, but are not limited to, Coliphage, *Salmonella* phage, *Listeria* phage, *Campylobacter* phage, *Bacillus* phage, *Enterococcus* phage, *Pseudomonus* phage, *Staphylococcus* phage, *Mycobacterium* phage, *Shigella* phage, *Streptococcus* phage, *Corynebacterium* phage, and *Vibrio* cholerae phage. Such phage are typically available from the American Type Culture Collection or can be isolated from nature, and can be used in the form of lyophilized pellets, for example.

Suitable antiviral agents are used in the methods and devices of the invention to kill the extracellular bacteriophage. These include, but are not limited to, ferrous salts, cuprous salts, leaf extracts, pomegranate rind extracts, and organic acids such as unsaturated fatty acids. Examples of antivirals are disclosed in International Publication No. WO 95/22254 and U.S. Pat. No. 5,840,308 (Jassim et al.).

Suitable bacterial helper cells are used to amplify the bacteriophage and preferably provide enzymes for detection. Such bacterial helper cells can be the same or different than the target bacteria. Preferably, they should be closely related to the target bacteria such that they can be infected by the chosen bacteriophage. Examples of bacterial helper cells include, but are not limited to, target bacteria such as *E. coli, Salmonella, Listeria, Campylobacter, Bacillus, Enterococcus, Pseudomonus, Staphylococcus, Mycobacterium, Shigella, Streptococcus, Corynebacterium*, and *Vibrio* bacteria, as well as attenuated versions thereof.

Such bacteriophage, antiviral agents, and bacterial helper cells are biological assay reagents as used herein. Other biological assay reagents that can be used in the devices and methods of the present invention include metabolic regulators, selective agents, proteins, antibodies, enzyme substrates, dyes, pigments, indicator chemistries, nutrients, or combinations thereof. Metabolic regulators can be added to induce particular detectable enzymes. Examples include, but are not limited to, isopropylthiogalactoside and glucose. Selective agents can be added to select growth of a desired bacteria. Examples include, but are not limited to, bile acids and certain dyes and pigments. Proteins can be added to neutralize the antiviral agents. Examples include, but are not limited to bovine serum albumin and egg albumin. Antibodies can be used to detect phage-specific proteins and internal proteins or other peptides. Examples include, but are not limited to polyclonal or monoclonal antibodies directed to specific proteins, such as the major capsid protein. Enzyme substrates can be used to detect enzymes released from the helper cells by the production of color, luminescence, or fluorescence. Examples include, but are not limited to, those disclosed in U.S. Pat. No. 5,958,675 (Wicks et al.). Nutrients can be added to support bacterial growth including helper bacterial cells. Examples include, but are not limited to, yeast extracts, inorganic salts, micronutrients, and other growth media or components thereof. Dyes and pigments can be added to assist in the visualization of plaques. Examples include, but are not limited to, those disclosed in U.S. Pat. No. 5,958,675 (Wicks et al.). Indicator chemistries, such as pH indicators, can be added to assist in the detection of enzyme reactions that utilize or produce hydrogen ions. Examples include, but are not limited to, sulfonphthaleins such as phenol red and bromthymol blue.

The device used to perform this assay is specially designed to contain the above-listed components to carry out the PAA. The device may have a number of components and/or compartments which allows these materials to be separated (e.g., in liquid-tight compartments) and mixed when desired to carry out an assay. An example of a device that can be used according to the present invention is disclosed in U.S. Pat. No. 5,067,051 (Ladyjensky), U.S. Pat. No. 3,290,017 (Davies), and U.S. Pat. No. 5,508,893 (Nowak).

The device components are compartmentalized by inserting seals (e.g., valves). Referring to FIG. 1, a device 10 includes at least two chambers 12 and 14 separated by a seal 16, which allows for communication between the two chambers (preferably, fluid communication) upon activation of the seal. Preferably, the activation can occur by rotating (e.g., tilting) the seal (hence, a rotatable seal), crushing the seal, or otherwise gating or opening the seal. More preferably, activation of the seal involves rotating the seal (e.g., turning it approximately 90° upon the application of pressure) such that the seal remains in one piece.

The body or walls of the device can be made from a variety of materials, particularly an organic polymeric material (e.g., polypropylene, polyethylene, polybutyrate, polyvinyl chloride, and polyurethane), that do not adversely react with the reagents within the device compartments. The device is preferably made of a flexible material, which can be transparent, translucent, or opaque. The seals can be made from a variety of materials, particularly an organic polymeric material (e.g., silicone, rubber, polyurethane, polyvinyl chloride), that do not adversely react with reagents within the device compartments. The seals can be in the form of membranes, discs, valves, etc. They are typically made of a more rigid material than that which forms the body of the device. They can be held in place in the body of the device using a variety of techniques, including chemical or mechanical techniques (e.g., ultrasonic welding or pressure fit). The body of the device may or may not have ends that may or may not be sealed or capped. Such end caps can be a part of the body of the device or a separate therefrom. For example, a cap made of the same or different material from that of the body can be used.

In preferred embodiments, the device includes at least three chambers, wherein at least two of which are separated by a seal that rotates upon activation. At least one of these chambers includes one or more biological assay reagents for detecting a microorganism. The assay reagent may be a liquid substance or a solid substance, such as a powder. Examples of assay reagents are described above. Various combinations of the biological assay reagents can be used in the devices of the invention. For example, in any one chamber a mixture of assay reagents can be used.

With continuing reference to FIG. 1, a device includes at least three chambers 12, 14, and 18 separated by seals 16 and 20, which allow for the communication between adjacent chambers. In at least one embodiment, the components include bacteriophage, an antiviral solution, and bacterial helper cells in separate chambers. Specifically, a first chamber 12 includes bacteriophage, a second chamber 14 includes an antiviral agent, and a third chamber 18 includes bacterial helper cells. As shown in FIG. 1, the second chamber 14 is preferably disposed between the first and third chambers. The second chamber 14 can be separated into two subchambers 22 and 24, each of which can include a different antiviral agent, separated from each other by a seal 26. The components may be mixed together by rotating the seal(s), which allows the components in two or more of the chambers to mix. The mixing of the components, for example, the antiviral solutions, can be done easily in this device. The antiviral component kills viruses but preferably does not harm the infected target bacteria.

In carrying out the present invention directed to a method for detecting microorganisms, the following steps are performed. A device as described above is provided. Preferably, the device includes at least two chambers separated from each other by an activatable seal, wherein at least one chamber includes a biological assay reagent. More preferably, the device includes at least three chambers separated from each other by seals, wherein a first chamber includes bacteriophage, a second chamber includes an antiviral agent, and a third chamber includes bacterial helper cells, wherein the second chamber is disposed between the first and third chambers. A sample suspected of including microorganisms, e.g., target bacterial cells, is added to the first chamber. If necessary, time is allowed for the sample to interact with any biological assay reagent present in the first chamber. For example, sufficient time is allowed for bacteriophage to infect target bacterial cells. Alternatively, the seal between one or more of the chambers is activated to allow contact between the reagent and the sample. Furthermore, other seals can be activated in sequence for the desired communication between reagents and sample. For example, the seal between the first and second chambers in the preferred device shown in FIG. 1 is activated (e.g., rotated) to allow contact between the antiviral agent and extracellular bacteriophage (i.e., bacteriophage that did not infect a microorganism in the sample). Subsequently, the seal between the second and third chambers is activated (e.g., rotated) to allow contact between the bacterial helper cells and the infected target bacterial cells. If necessary, the bacterial helper cells and the infected bacterial cells can be incubated for a sufficient time to amplify the bacteriophage and/or generate a bacteriophage dependent signal (e.g., luminescence).

The presence or absence of the target microorganisms in the sample can then be detected. Detection can involve turbidity changes, plaque formation, as well as color, luminescence, or fluorescence formation using standard techniques and instruments.

For the detection of bacteria, methods other than a phage-based detection method can also be used according to the present invention. For example, a thermal-stable nuclease in a bacteria such as coagulase positive *Staphylococcus* can be detected using a device that includes a biological assay reagent such as growth media in a first chamber into which a sample suspected of containing the target bacteria is introduced for incubation and lysing, and a second biological assay reagent such as an indicator dye in an adjacent second chamber. As another example, a protein such as galactosidase from coliforms can be detected using a device that includes growth media in a first chamber into which a sample suspected of containing the target bacteria is introduced for incubation, a galactosidase-inducing agent in an adjacent second chamber, and an enzyme substrate in an adjacent third chamber for detection.

For the detection of microorganisms other than bacteria, various known methods can be adapted for use in the devices according to the present invention. For example, yeast can be detected by introducing a sample suspected of containing yeast into a device containing a first chamber that includes growth media for yeast and antibiotics to kill any bacteria in the sample, and then into a second chamber containing a substrate for detecting alkaline phosphatase.

EXAMPLES

The following examples are offered to aid in understanding of the present invention and are not to be construed as limiting the scope thereof. Unless otherwise indicated, all parts and percentages are by weight

Example 1

Phage Amplification Device

A device was constructed from a cylindrical flexible plastic (polypropylene) tube that was 128 mm long, with an outside diameter of 6.35 mm, and with a tube wall thickness of 0.5 mm (refer to FIG. 1). Removable solid plastic stoppers were used to close the device at both a bottom end and a top end. The device was separated into four chambers by rotatable silicone rubber disk-shaped valves having a thickness of 1.9 mm and a diameter of 5.85 mm. The valves initially were in a "closed position" (perpendicular to the tube wall and sealing adjacent chambers from each other), but could be rotated about 90° to an "open position" (to connect adjacent chambers) by finger twisting and manipulation of the outside surface of the device. The four chambers of the device were comprised of Chamber 12 (618 mm$^3$) at the top of the tube, Chamber 22 (309 mm$^3$) adjacent to Chamber 12, Chamber 24 (538 mm$^3$) adjacent to Chamber 22, and Chamber 18 (1747 mm$^3$) at the bottom of the tube. Valve 26 separated Chambers 22 and 24, Valve 16 separated Chambers 12 and 22, and Valve 20 separated Chambers 24 and 18.

Example 2

Phage Amplification Device

A second device was constructed from a cylindrical flexible plastic (polypropylene) tube that was 128 mm long, with an outside diameter of 8.4 mm, and with a tube wall thickness of 0.5 mm (refer to FIG. 1). Removable solid plastic stoppers were used to close the device at both a bottom end and a top end. The device was separated into 4 chambers by rotatable SANTOPRENE™ thermoplastic rubber disk-shaped valves having a thickness of 1.5 mm and a diameter of 7.9 mm. The valves initially were in a "closed position" (perpendicular to the tube wall and sealing adjacent chambers from each other), but could be rotated about 90° to an "open position" (to connect adjacent chambers) by finger twisting and manipulation of the outside surface of the device. The 4 chambers of the device were comprised of Chamber 12 (1471 mm$^3$) at the top of the tube, Chamber 22 (588 mm$^3$) adjacent to Chamber 12, Chamber 24 (686 mm$^3$) adjacent to Chamber 22, and Chamber 18 (2549 mm$^3$) at the bottom of the tube. Valve 16 separated Chambers 12 and 22, Valve 26 separated Chambers 22 and 24, and Valve 20 separated Chambers 24 and 18.

Example 3

Detection and Enumeration of Bacteria

A device for phage amplification (PAD) was constructed as described in Example 1 for use in the detection and enumeration of bacteria in a sample. However, during construction a 4.8 mM solution (0.5 ml) of ferrous sulfate (Product No. 2070-01, J. T. Baker, Phillipsburg, N.J.) in deionized water was added to Chamber 24 to serve as an antiviral component and a 13% aqueous solution (0.25 ml) of pomegranate rind extract (PRE) (prepared as described in International Publication No. WO 95/22,254 (Stewart, et al.)) was added to Chamber 22 to serve as an antiviral component. Following construction, a pellet of lyophilized E. coli, ATCC 13706 bacteria (approximately 1×10$^8$ cfu/ml) was added to Chamber 18 to serve as bacteria "helper cells." Chamber 12 was left empty to receive the test sample and all valves were set initially in a "closed position."

An overnight culture of E. coli, ATCC 13706 containing 1×10$^8$ cfu/ml was diluted ten-fold stepwise in Lambda buffer (prepared as described in Example 4 of U.S. Pat. No. 5,498,525 (Rees, et al.)) and then introduced into Chamber 12 so that the chamber contained approximately 0.1 ml of culture solution. To this sample was added 10 µl of a Nutrient Broth (Product No. 4311479, BBL, Cockysville, Md.) suspension of bacteriophage [ϕX 174 (ATCC 13706-B1)] containing 1×10$^{11}$ pfu/ml. The bacteriophage was allowed to adsorb to the bacteria for 10 minutes at 37° C. in an incubator. Valve 26 was then opened and the antiviral components of Chambers 22 and 24 were allowed to mix for 2 minutes at 23° C. Non-adsorbed bacteriophage were then inactivated by opening Valve 16 and allowing the antiviral solution to mix with the contents of Chamber 12 for 5 minutes at 23° C. The resulting solution was then neutralized by opening Valve 20 and combining the solution with the bacteria pellet in Chamber 18 for 5 minutes at 23° C. The final solution in the device was transferred to a sterile plastic screw cap tube (16 mm×100 mm) that contained 2.5 ml of top agar (Standard Nutrient Broth top agar media for agar overlay methods) held in a molten state at 42° C. The top agar solution was poured onto a bottom agar plate (Standard Nutrient Agar) and incubated at 37° C. for 24 hours. The number of plaques was counted at 6 hours and 24 hours, and results for the series of 8 dilutions (10$^{-3}$ to 10$^{-10}$) are provided in Table 1.

A negative Control Sample (C-1) was run in the same manner as described above, except that no E. coli bacteria were added to the initial Lambda buffer sample in order to demonstrate the effectiveness of bacteriophage kill by the antiviral components. A positive Control Sample (C-2) was run in the same manner as described above (10$^{-3}$ dilution), except that no antiviral components were utilized. Additionally, each stepwise diluted sample of the E. coli culture was plated onto standard PETRIFILM™ E.C. plates (3M Company, St. Paul, Minn.) and incubated (24 hours at 37° C.) according to manufacturer's directions. The results from the Control Samples and from the PETRIFILM™ plate assays are also provided in Table 1.

TABLE 1

Detection and Enumeration of Bacteria (E. coil)

| | | "PAD Method" (pfu$^1$) | | "PETRIFILM ™ Plate Method" 24 hours |
|---|---|---|---|---|
| Run | Dilution | 6 Hours | 24 hours | (cfu$^2$) |
| 1 | 10$^{-3}$ | TNTC$^3$ | TNTC | TNTC |
| 2 | 10$^{-4}$ | TNTC | TNTC | TNTC |
| 3 | 10$^{-5}$ | 400 | 2000 | TNTC |
| 4 | 10$^{-6}$ | 60 | 200 | 391 |
| 5 | 10$^{-7}$ | 5 | 24 | 49 |
| 6 | 10$^{-8}$ | 1 | 12 | 12 |
| 7 | 10$^{-9}$ | 0 | 0 | 0 |
| 8 | 10$^{-10}$ | 0 | 0 | 0 |
| C-1 | — | 0 | 0 | 0 |
| C-2 | 10$^{-3}$ | TNTC | TNTC | TNTC |

$^1$pfu = plaque forming units
$^2$cfu = colony forming units
$^3$TNTC = to numerous to count The data from Table 1 show that the results (reduction of pfu at 6 hours and 24 hours) utilizing the device of Example 1 correlate very well with the results (reduction of cfu at 24 hours) obtained from standard PETRIFILM™ plate assays. It was noted that cfu on the PETRIFILM™ plate assays were not observed until after about 12 hours.

Example 4

Detection and Enumeration of Bacteria

A device for phage amplification (PAD) as described in Example 2 was filled with reagents as described in Example 3, and was then utilized for the detection and enumeration of *E. coli* bacteria as described in Example 3. The number of pfu ("PAD Method") and the number of cfu ("PETRIFIM™ Plate Method") were counted and results for the series of 8 dilutions ($10^{-3}$ to $10^{-10}$) are provided in Table 2.

TABLE 2

Detection and Enumeration of Bacteria (*E. coil*)

| Run | Dilution | "PAD Method" (pfu) | | "PETRIFILM ™ Plate Method" 24 hours |
| --- | --- | --- | --- | --- |
| | | 6 Hours | 24 hours | (cfu) |
| 1 | $10^{-3}$ | TNTC | TNTC | TNTC |
| 2 | $10^{-4}$ | 1000 | TNTC | TNTC |
| 3 | $10^{-5}$ | 113 | 200 | 1540 |
| 4 | $10^{-6}$ | 43 | 135 | 360 |
| 5 | $10^{-7}$ | 1 | 4 | 16 |
| 6 | $10^{-8}$ | 0 | 1 | 2 |
| 7 | $10^{-9}$ | 0 | 0 | 1 |
| 8 | $10^{-10}$ | 0 | 0 | 0 |
| C-1 | — | 0 | 0 | 0 |
| C-2 | $10^{-3}$ | TNTC | TNTC | TNTC |

The data from Table 2 show that the results (reduction of pfu at 6 hours and 24 hours) utilizing the device of Example 2 correlate very well with the results (reduction of cfu at 24 hours) obtained from standard PETRIFILM™ plate assays. It was noted that cfu on the PETRIFILM™ plate assays were not observed until after about 12 hours.

The entire disclosure of all patents, patent applications, and publications are incorporated herein by reference as if each were individually incorporated. Various modifications and alterations of this invention will become apparent to those skilled in the art without departing from the scope and spirit of the invention. It should be understood that this invention is not intended to be unduly limited by the illustrative embodiments and examples set forth herein and that such examples and embodiments are presented by way of example only. The scope of the invention is intended to be limited only by the claims set forth herein as follows.

What is claimed is:

1. A method for detecting the presence or absence of bacteria, the method comprising:
    providing a device comprising at least three chambers separated from each other by seals, wherein a first chamber includes bacteriophage, a second chamber includes an antiviral agent, and a third chamber includes bacterial helper cells, wherein the second chamber is disposed between the first and third chambers;
    adding a sample suspected of including target bacteria to the first chamber comprising bacteriophage;
    allowing the bacteriophage to infect the target bacteria;
    activating the seal between the first and second chambers to allow contact between the antiviral agent and extracellular bacteriophage;
    activating the seal between the second and third chambers to allow contact between the bacterial helper cells and the infected target bacteria;
    incubating the bacterial helper cells and the infected bacteria; and
    detecting the presence or absence of the target bacteria in the sample.

2. The method of claim 1 wherein the second chamber is separated into two subchambers separated from each other by a seal.

3. The method of claim 2 wherein the two subchambers of the second chamber each include an antiviral agent.

4. The method of claim 3 wherein the seal between the two subchambers is activated to allow the two antiviral agents to mix prior to contacting the antiviral agents with the extracellular bacteriophage.

* * * * *